(12) United States Patent
Zaias et al.

(10) Patent No.: US 6,565,535 B2
(45) Date of Patent: May 20, 2003

(54) MEDICAL INFUSION AND ASPIRATION SYSTEM

(76) Inventors: Nardo Zaias, 660 S. Shore Dr., Miami Beach, FL (US) 33141; Gregory F. Gilbert, 7321 Roseville Rd., Ste. 10, Sacramento, CA (US) 95742

( * ) Notice: Subject to any disclaimer, the term of this patent is extended or adjusted under 35 U.S.C. 154(b) by 0 days.

(21) Appl. No.: 09/881,828

(22) Filed: Jun. 15, 2001

(65) Prior Publication Data

US 2002/0007139 A1 Jan. 17, 2002

Related U.S. Application Data

(60) Provisional application No. 60/212,134, filed on Jun. 16, 2000.

(51) Int. Cl.$^7$ ................................................. A61M 1/00
(52) U.S. Cl. .................. 604/152; 604/131; 604/30; 604/31; 604/35; 604/189; 128/DIG. 13
(58) Field of Search ................ 604/27, 29, 30–35, 604/43, 519, 65–67, 80, 81, 131, 134, 135, 151, 152, 154, 155, 187, 218, 224, 245, 537, 902, 186, 189, 198; 128/DIG. 12, DIG. 13, DIG. 1; 600/561–563, 565, 568

(56) References Cited

U.S. PATENT DOCUMENTS

| | | | | |
|---|---|---|---|---|
| 4,435,173 A | * | 3/1984 | Siposs et al. | 128/DIG. 1 |
| 4,978,335 A | * | 12/1990 | Arthur, III | 128/DIG. 1 |
| 5,317,506 A | * | 5/1994 | Coutre et al. | 128/DIG. 13 |
| 5,531,679 A | * | 7/1996 | Schulman et al. | 128/DIG. 12 |
| 5,800,405 A | * | 9/1998 | McPhee | 604/135 |
| 5,882,338 A | * | 3/1999 | Gray | 604/131 |
| 5,954,689 A | * | 9/1999 | Poulsen | 604/211 |
| 6,248,093 B1 | * | 6/2001 | Moberg | 128/DIG. 12 |
| 6,269,340 B1 | * | 7/2001 | Ford et al. | 604/19 |
| 6,387,077 B1 | * | 5/2002 | Klibanov et al. | 128/DIG. 1 |
| 6,406,455 B1 | * | 6/2002 | Willis et al. | 604/191 |
| 6,423,035 B1 | * | 7/2002 | Das et al. | 604/155 |

* cited by examiner

Primary Examiner—Brian L. Casler
Assistant Examiner—Cris L. Rodriguez (57) ABSTRACT

The present invention is a medical infusion and aspiration system capable of accurate pulsate delivery of high rates off flow. The system comprises a pumping mechanism, a cassette housing, a plunger and a cartridge having a reservoir area, an encoded area and a neck opening for connection to an infusion tube with an in-line sensor area where sampling probes are located. The cartridge is in threaded connection with the housing and the plunger fits within the reservoir area. The encoded area allows for an optical or electromagnetic strip containing information as to the contents and uses of the contained reagent, thus minimizing dosage mistakes. A motor is linked to the housing and causes bi-directional rotation of the plunger in relation to the housing. The plunger rotation breaks the forces of inertia and slip-stick as well as eliminate backlash. The system eliminates the need for withdrawing medicine with a needle and achieves extraordinary accuracy without error correcting software or expensive volumetric measurement and control systems.

17 Claims, 6 Drawing Sheets

MEDICAL INFUSION AND ASPIRATION SYSTEM

CROSS REFERENCE WITH OTHER APPLICATIONS

This application claims the benefit of U.S. Provisional Patent Application No. 60/212,134, filed Jun. 16, 2000.

FIELD OF INVENTION

This invention relates to medical systems, and more specifically, to a medical infusion and aspiration system which provides a highly accurate, easily operated, disposable and reliable way to deliver any type of liquid or reagent with few moving parts.

BACKGROUND

There exists numerous ways to pump and aspirate liquids, beginning with a doubly open pipette and progressing to highly sophisticated electromechanical software correcting systems with many moving parts and error checking systems. Improvements in pumping systems have centered on the use of electronic controls to compensate for the mechanical limitations of current pumping systems, which generally use non-rigid materials. Many of these more sophisticated pumping mechanisms have valves and chambers that disturb the reagents normally used in such devices. The basic problem has been that in medical and other applications, there have been only a few instances where pulsatile infusion is required, and in those instances, the conventional pumping systems merely rely upon starting and stopping the pump to achieve a pulsatile regimen. Furthermore, the approach to accuracy in pumping has been to slow the device so that a precise metering could take place, which is not desired in several new medical treatments. Current products only offer pump accuracy specifications of plus- or minus 2 to 5 percent, over the entire reservoir, nor for each pulse, thereby making individual deliveries much less accurate. Thus, since there has been no apparent need for a device which could both be accurate, and still pump at a relatively high rate of flow, the field had not included a pump which can be both accurate in a pulsatile delivery, and have high rates of flow. The use of higher volumes in delivering medicines are often not medically indicated and many of the current systems have resorted to averaging out individual error to get a reportable accuracy level which is tolerable but never optimal. In fact, reporting and delivering accuracy over the entire reservoir does not deliver what the newer treatments now desire, and leads the user to believe in individual accuracy of each aliquot which in not in fact delivered.

In addition, many of the problems associated with mistakes in the delivery of medicines into patients have resulted from errors in the concentrations of the active reagent. Furthermore, most medicines have a relationship to the weight of a patient, such that their drug labels give levels of optimal administration, which should not be exceeded in the ordinary practice of medicine. Other sources of inaccurate concentrations in the delivery of medicines are the forces of ionization and collection of medicines on the surfaces of the bag or container used as a reservoir to store and deliver the medicine. The medicine can also collect on the sides of the container, and only be delivered in a relatively short period of time.

In addition to the problems discussed above, most medicines have protein or other complex molecules which are relatively easily damaged with any type of gate, valve or force which causes shearing upon the opening and closing of mechanism to stop flow. These proteins have the ability to aggregate and become ineffective, thereby giving to the patient a medicine which has changed in its effective concentration. Shear and aggregation can also occur with having flows in areas which have a high pressure.

Furthermore, many current pumping devices use syringes and have no ability to overcome the natural slip-stick or chatter associated with the storage of energy in the elastic and pliable surfaces and structures, allowing for the syringe moving face ("Plunger") to move forward in irregular motions. Hysteresis and the natural tendency of plungers not to move until a force overcomes the inertia and sticking forces cause delivery of most syringe pumps to be sporadically subject so differing levels of sticking (sticktion). When these devices overcome this inertia and hysteresis, they tend to overrun and deliver at different speeds. In addition, many pumping devices vary their delivery according to the viscosity of the fluid being distributed.

Another drawback with current infusion devices is that most medicines must be withdrawn from a container, and put into the system for administration. This process requires withdrawing the medicine with a needle and then infusing the medicine into a bag or other container. The use of needles presents a hazard to the user and also introduces losses of reagent during the priming of current infusion devices.

What is needed is a medical infusion and aspiration system that avoids the disadvantages of pre-existing medical infusion and aspiration devices, that is accurate in pulsatile delivery, that is capable of high rates of flow, that provides a means to automatically avoid errors in concentrations, reagent and medicine type, that avoids the problem of shear, and other medicine degrading pressure problems, that avoids the slip-stick, chatter, overruns, and the problem of hysteresis by breaking the seating forces in a lateral motion, that does not vary the delivery profile by the viscosity of the reagent, that avoids the tendency of reagents to separate when in a diluted environment, that is inexpensive and may be used by the manufacturer in glass lined or plastic, as both the pumping cartridge and the shipping and storage cartridge, that eliminates avoids loss of reagent in the priming of the infusion device and the need for withdrawing the medicine with a needle, and that achieves extraordinary accuracy without error correcting software or expensive volumetric measurement and control systems.

SUMMARY

Accordingly, the present invention is a medical infusion and aspiration system capable of accurate pulsatile delivery at high rates of flow. Another important characteristic of the invention is that the device provides a means to automatically avoid errors in concentration, reagent and medicine type, avoids the problems of shear and other medicine degrading pressure problems. The system also avoids the slip-stick, chatter, overruns, and the problem of hysteresis by breaking the seating forces in a lateral motion that does not vary the delivery profile by the viscosity of the reagent. The system also eliminates the tendency of reagents to separate when in a diluted environment. Other important characteristics of the invention include disposability, inexpensive cost and use by the manufacturer in glass lined or plastic, as both the pumping cartridge and the shipping and storage cartridge thus avoiding loss of reagent in the priming of an infusion device. The current invention also eliminates the need for withdrawing the medicine with a needle and achieves extraordinary accuracy without error correcting software or expensive volumetric measurement and control systems.

The current invention consists of a cassette cartridge pumping and aspirating system. The cassette cartridge contains a plunger, a reservoir area where the reagent is filled, a neck opening for the connection of the cartridge to a tube which travels to where the infusion takes place, and an in-line sensor area where probes for sampling are located. The in-line area probes are used to provide input to a pumping device. The current invention has only one moving part in relation to the delivery mechanism. Simplicity allows for more accuracy and lower costs. It also allows for a single handed adaption of the cassette to the pumping device, freeing the other hand and avoiding accidental sticking with "sharps" such as needles which are contaminated with blood or other materials.

In a preferred embodiment, the cartridge is cylindrical in shape and has a reservoir area, a neck opening, and encoded area. The cartridge may be made of glass, plastic steel or ceramics. It is preferable that the outer surface of the cartridge be threaded. The reservoir area is preferably used for containing a reagent and may be pre-filled, thereby enabling the seller to market pre-filled reagent cartridges. The preferred embodiment eliminates expensive residue that is thrown away with the transportation bottle, as prefilling allows for no waste. Pumps which may be re-inserted can store the unused reagent for an appropriate period of time in the cassette.

The neck opening is preferably located at the bottom surface of the cartridge and sized to connect an infusion tube to the cartridge. Any conventional tube connection device may be used to connect the infusion tube to the cartridge. The cartridge also has a cap and container top which allows the cartridge to act as the storage vessel for the reagent, and thereby avoid additional steps of filling, mixing, measuring or wasting reagent in the handling of the fluid.

In the preferred embodiment of the invention, an optical or electromagnetic strip is located within an encoded area on the cartridge. When the cartridge is filled, an optical or electromagnetic strip with information on the contents and uses of the reagent is placed in the encoded area. The encoded area is preferably located on the outer surface of the cartridge in the area that is first inserted the housing. When the cartridge is placed in the device, it is preferable that the rotational action causes the encoded area to be well aligned and easily read with the uniform motion of screwing the cartridge into place. The preferred rotation, pre-determined position of the encoded area, and the ease of programming a unique character to each cartridge allows the reagent to be mistake limiting. Furthermore, the preferred embodiment system requires a weight to be entered into a pumping device for each patient, thus greatly reducing the incidence of errors. Any conventional method of storing and retrieving data from the encoded area are preferably included in the present system to limit the incidence of errors. It is preferable that the encoded area comes into close proximity with a reading system as the cartridge is loaded or is first used. The reading system may be any commercially available system capable of reading the encoded area. A medical device stores and uses the encoded information in its operations, including a means to limit the profile of the infusion allowed without further intentional override of the profile.

In the preferred embodiment, the housing consists of a cylindrical tube that is sealed at the upper end and made from plastic. The bottom of the housing is preferably open and the inner surface of the housing is preferably threaded and sized to receive the cartridge. A plunger is preferably connected to the sealed end and is suspended in alignment with the central axis of the cylindrical tube. In the preferred embodiment, there is a plurality of openings cut through the housing to allow for normally trapped air to be exhausted as the plunger either advances or retards. The plurality of openings also creates an inspection window within the housing allowing access to the optical or electromagnetic strip within the encoded area. A lip at the bottom of the housing provides for a manually removable cover used to protect the cartridge from contamination or damage to the plunger. When the cartridge is engaged in the housing, the cartridge is locked into place by the rotational engagement of the threads. The locking of the meshed threads makes an accidental infusion by dropping or pressing on the plunger virtually impossible. The cartridge will not siphon out of the pump, or accidentally deliver fluid when dropped or pushed against.

The preferred plunger is a piston-type plunger and is preferably connected to the sealed end of the housing and is aligned with the central axis of the housing. The plunger head is preferable sized to fit the reservoir opening, so there is very little dead space thus resulting in very little loss of reagent in the final stroke or at the end of treatment.

In the preferred embodiment, a pumping mechanism is used to rotate the plunger within the cassette. The pumping mechanism comprises a gear linkage, a motor and a pumping device. The pumping mechanism may be actuated by any motor which rotably moves the plunger or housing. The present invention allows for direct drive, stepper motor, spring or band action motor, or hand articulation to deliver the desired plunger rotation. The "motor" may be even a coordinated hand-eye movement or movement to a series of "click" points. In a preferred embodiment, the plunger rotates in relation to the walls of the cassette housing.

In the preferred embodiment, the cartridge, when placed in the housing, causes the piston plunger to move both forward and aft to aspirate or infuse, as well as rotate within the Cassette to break the forces of inertia and slip-stick as well as eliminate backlash. Because the device avoids slip-stick, chatter and the forces of hysteresis, and has no gates or valves, it is designed to also be used in a bi-directional application, such as one of the preferred embodiments herein, where the precise amount being withdrawn may be distributed, equally or in successive steps of precise delivery, or the precise amount withdrawn re-inserted into the patient to the "zero" point.

A sensor area located in the infusion tube contains probes designed to determine the chemical components and levels of desired substrates in the aspirated fluids. The information obtained by the probes relayed to the pumping device and is used to control or limit the infusion profile.

The bi-directional accuracy of the present invention allows the system to be used with any number of probes. It is preferable that the probes measure the properties of a sample, such as blood, and then allow the prevent invention to re-infuse that sample back into the patient after it has been tested, or if desired, by second flow direction, deposit that blood into a separate container or depository.

The present invention also includes a pumping device. The pumping device preferably has one, two, three or more sources of input. The preferred pumping device includes, but is not limited to, an input system to drive the device, a sensor input for in-line measurement of substrates, an in-line occlusion pressure sensing system and/or input from the reading of the encoded area. The sensor input receives signals from the in-line sensor probes. The in-line occlusion pressure sensing system determines the line pressure or back pressure on the motor. Other traditional pump features are intended to be incorporated into the pumping device. In the preferred embodiment, the Rotational Velocity exceeds the Axial Velocity, although with sufficient diameter the difference in Rotational travel to Axial travel could be adjusted for the flow characteristics of the fluid to be infused and aspirated.

It is preferable that a second cassette and housing may be coupled and driven either independently or in mechanical linkage with a cassette housing so as to have as many infusion profiles, either in succession or concurrently as is desired for the given flow profiles and applications.

Since the cartridge is also the pumping system, each time the cartridge is used, it is replaced, and the entire wearing aspects of the pumping system are replaced. The product life cycles are much greater. The entire fluid handling system is replaced with each use and sterilization and cleaning of parts is eliminated.

The purpose of the present invention is to provide a system of quantitative chronoendocrinology, a term coined by the inventor. The apparent benefit to having pulses of almost any medicine, as an additional means for delivery, was deemed by the Inventors to be a valid approach to medical infusion for any and perhaps all forms of infusion therapy. Part of the invention claimed is the use of the device in sequence of infusions which, while in the aggregate the amount medicine used is less, but by virtue of the pulses, accomplishes additional medical results.

DESCRIPTION OF THE DRAWINGS

A preferred embodiment of the present invention is further described in connection with the accompanying drawings, in which.

DETAILED DESCRIPTION OF THE INVENTION

The present invention is a medical infusion and aspiration system capable of accurate pulsatile delivery at high rates of flow. The present invention provides a means to automatically avoid errors in concentration, reagent and medicine type, and avoids the problems of shear and other medicine degrading pressure problems. The system also avoids the slip-stick, chatter, overruns, and the problem of hysteresis by breaking the seating forces in a lateral motion that does not vary the delivery profile by the viscosity of the reagent. The system also avoids loss of reagent in the priming of a separate infusion device and eliminates the tendency of reagents to separate when in a diluted environment. The invention is disposable, inexpensive and may be used by the manufacturer in glass lined or plastic, as both the pumping cartridge and the shipping and storage cartridge. The current invention also eliminates the need for withdrawing the medicine with a needle and achieves extraordinary accuracy without error correcting software or expensive volumetric measurement and control systems.

In general, the current invention comprises a cassette cartridge pumping and aspirating device. The cassette cartridge pumping and aspiration system consisting of a cartridge, a housing, a plunger, a reservoir area where the reagent is contained, a neck opening for the connection of the cartridge to a tube which travels to where the infusion takes place, and an in-line area where probes for sampling are located. The in-line area probes are used to provide input to a pumping device. The current invention has only one moving part in relation to the delivery mechanism and this simplicity allows for more accuracy and lower costs. It also allows for a single handed adaption of the cassette to the pumping device, freeing the other hand and avoiding accidental sticking with "sharps" such as needles which may be contaminated with blood or other materials.

Figure 1:
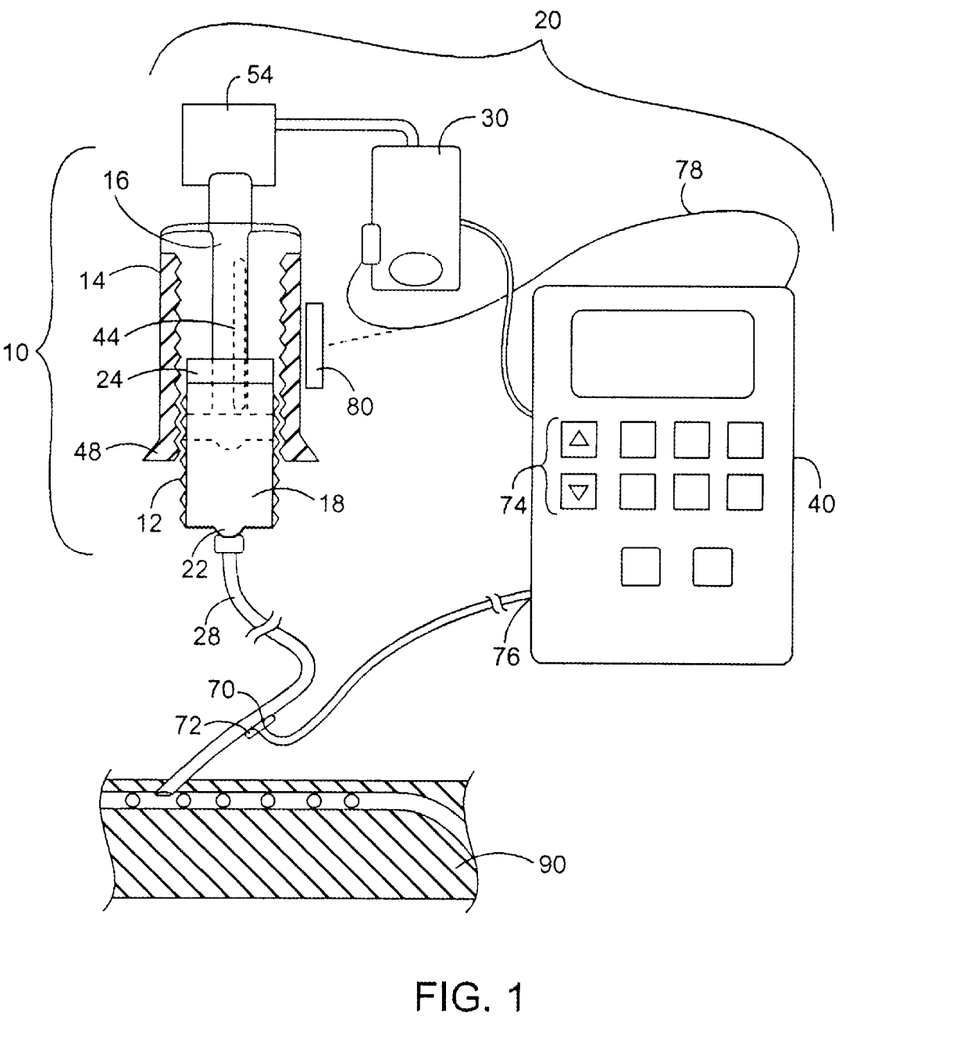
FIG. 1 is a perspective view of a preferred embodiment of the medical infusion and aspiration system.

Referring now to the figures, FIG. 1 is a perspective view of an embodiment of the invention showing a cassette 10, a pumping mechanism 20 and a motor 30. The cassette further comprises a cartridge 12, a housing 14, and a plunger 16.

Figure 2:
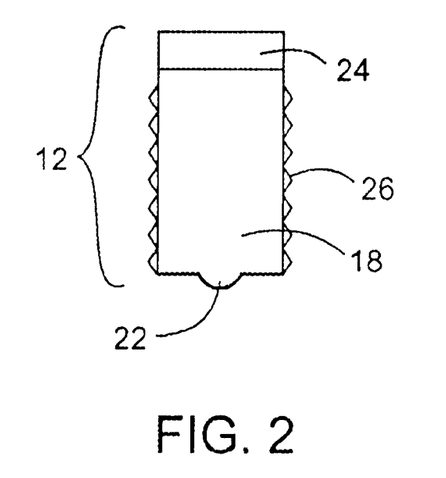
FIG. 2 is a perspective view of a preferred embodiment of the cartridge.

In a preferred embodiment, as best seen in FIGS. 1 and 2, the cartridge 12 is cylindrical in shape and has a reservoir area 18, a neck opening 22 and encoded area 24. The cartridge 12 is preferably made from glass or plastic. For high-pressure situations, it is preferable that the cartridge 12 be made of steel or ceramics. It is preferable that the outer surface of the cartridge be threaded 26. Any standard or metric thread size may be used.

The reservoir area 18 is preferably used for containing a reagent. The reservoir area 18 may be pre-filled, thereby enabling the seller to market pre-filled reagent cartridges. The preferred embodiment eliminates expensive residue that is thrown away with the transportation bottle, as pre-filling allows for no waste. Pumps which may be re-inserted can store the unused reagent for an appropriate period of time in the cassette.

The neck opening 22 is preferably located at the bottom surface of the cartridge 12. The neck opening 22 is preferably sized to connect an infusion tube 28 to the cartridge 12. Any conventional tube connection device may be used to connect the infusion tube 28 to the cartridge 12. The opposite end of the infusion tube 28 is connected to a vein 90.

It is preferable that the cartridge 12 also contain a cap and container top which allows the cartridge 12 to act as the storage vessel for the reagent, and thereby avoid additional steps of filling, mixing, measuring or wasting reagent in the handling of the fluid.

In the preferred embodiment of the invention, an optical or electromagnetic strip is located within an encoded area 24 on the cartridge 12. When the cartridge 12 is filled, an optical or electromagnetic strip with information on the contents and uses of the reagent is placed in the encoded area 24. The encoded area 24 is preferably located on the outer surface of the cartridge 12 in the area that is first inserted the housing 14.

It is preferable that optical reading of a bar code or other reading of the encoded area 24 will minimize dosage mistakes, as each cartridge can set the maximum allowable dose or delivery. When the cartridge: 12 is placed in the system, it is preferable that the rotational action causes the encoded area 24 to be well aligned and easily read with the uniform motion of screwing the cartridge 12 into place. The preferred rotation, pre-determined position of the encoded area 24, and the ease of programming a unique character to each cartridge 12 allows the reagent to be mistake limiting. Furthermore, the preferred embodiment system requires a weight to be entered into a pumping device 40 for each patient, thus greatly reducing the incidence of errors. Any conventional method of storing and retrieving data from the encoded area are preferably included in the present system to limit the incidence of errors.

It is preferable that the encoded area 24 comes into close proximity with a reading system as the cartridge 12 is loaded or is first used. The reading system may be any commercially available system capable of reading the encoded area 24. A medical device stores and uses the encoded information in its operations, including a means to limit the profile of the infusion allowed without further intentional override of the profile.

Figure 3:
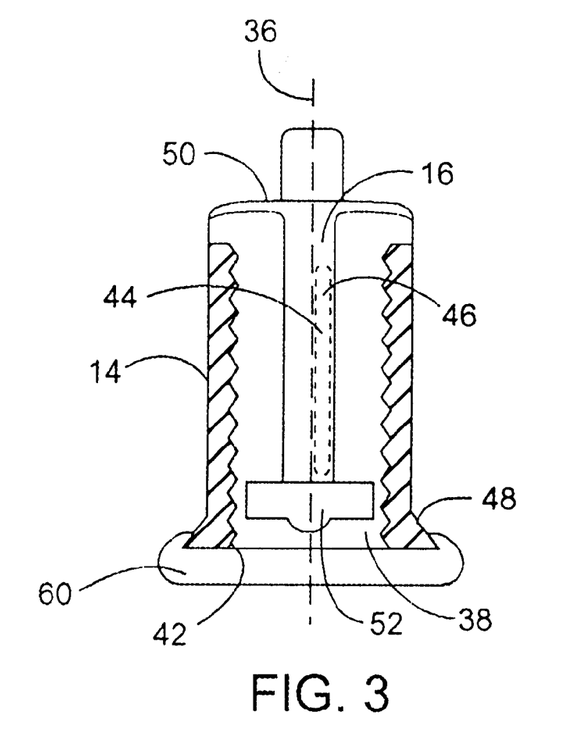
FIG. 3 is a perspective view of a preferred embodiment of the housing and plunger.

In the preferred embodiment, the housing 14 consists of a cylindrical tube that is sealed at the upper end, as shown in FIG. 3. The housing 14 is preferably made of plastic, however, any suitable commercially available material may be used. The bottom 38 of the housing is preferably open and the inner surface 42 of the housing is threaded. Any standard or metric thread size may be used. A plunger 16 is preferably connected to the sealed end 50 and is suspended in alignment with the central axis 36 of housing 14. The housing 14 is sized to threadedly receive the cartridge 12. In the preferred embodiment, there is a plurality of openings 44 cut through the housing 14 parallel to the central axis 36 of housing 14. These openings 44 allow for normally trapped air to be exhausted as the plunger 16 either advances or retards. The plurality of openings 44 also creates an inspection window 46 within the housing 14. The inspection window 46 also allows access to the optical or electromagnetic strip within the encoded area 24. A lip 48 at the bottom 38 of the housing 14 provide for a manually removable protective cap 60 used to protect the cartridge from contamination or damage to the plunger 16. The housing 14 may be made in a clamshell or disassembled manner for easy withdrawal.

When the cartridge 12 is engaged in the housing 14, the cartridge 12 is locked into place by the rotational engagement of the threads 26, 42. The locking of the meshed threads makes an accidental infusion by dropping or pressing on the plunger virtually impossible. The cartridge 12 will not siphon out of the pump, or accidentally deliver fluid when dropped or pushed against.

The preferred plunger 16 is a piston-type plunger and is made from plastic, however, any type of non-reactive material may be used. The plunger 16 is preferably connected to the sealed end 50 of the housing 14 and is aligned with the central axis of the housing. The plunger head 52 is preferable sized to fit within the reservoir area 18, so there is very little dead space thus resulting in very little loss of reagent in the final stroke or at the end of treatment.

The plunger 16 and reservoir area 18 configuration may have a larger diameter in relationship to the depth the plunger travels, or a very small diameter and longer plunger travel, depending upon the flow characteristics desired for the application. In very viscous fluids, a different diameter would be helpful for both storage and delivery reasons.

In the preferred embodiment, a pumping mechanism 20 is used to rotate the plunger 16 within the cassette 10. The pumping mechanism 20 comprises a gear linkage 54, a motor 30 and a pumping device 40. The pumping mechanism 20 may be actuated by any motor which rotably moves the plunger 16 or housing 14. The present invention allows for direct drive, stepper motor, spring or band action motor, or hand articulation to deliver the desired plunger rotation. The "motor" may also be a coordinated hand-eye movement or movement to a series of "click" points. In a preferred embodiment, the plunger 16 rotates in relation to the walls of the cassette housing 14.

In one embodiment, a motor 30 with either electromechanical or mechanical operation is attached to the gear or drive which in turn causes a rotation of the plunger 16 and both lateral and axial movement of the plunger 16. The motor 30 is controlled by predetermined settings which may be inputted into a pumping device by the operator to cause the pumping and aspiration actions to take place as desired. In the case of a mechanical motor, the settings may be made by a spring-like mechanism, with the number of turns and speed of the mechanism being governed by a simple clock mechanism.

The design of the motor 30 and assembly allow the pump mechanism 20 to be put above, at, or below the heart level, with no resulting change in the delivery profile. This allows the pump mechanism 20 to be worn or enclosed in several different tamper-proof or patient access limiting configurations.

The planes formed by the inner surface 42 of the housing and the outer surface 26 of the cartridge are positioned so as to allow the plunger 16 to begin turning as it is first attached, or after it is attached to the cassette housing 14. The plunger 16 may extend beyond the line of the housing 14 for purposes of easy snap-in connection and alignment of the cassette 10. The number of turns per meter or inch are adjusted to provide the desired rate of flow in both directions. The diameter of the cassette and its separate housing are adjusted to provide different flow rates and to adjust for any necessary fluid dynamics which might be necessary to pump highly viscous liquids or pump fluids at high flow rates.

As the plunger 16 is rotationally turned, the device infuses or aspirates liquid, depending on the rotational direction of the plunger. The rotational movement of the present invention allows for bi-directional movement and provides accurate infusion or aspiration.

Figure 4:
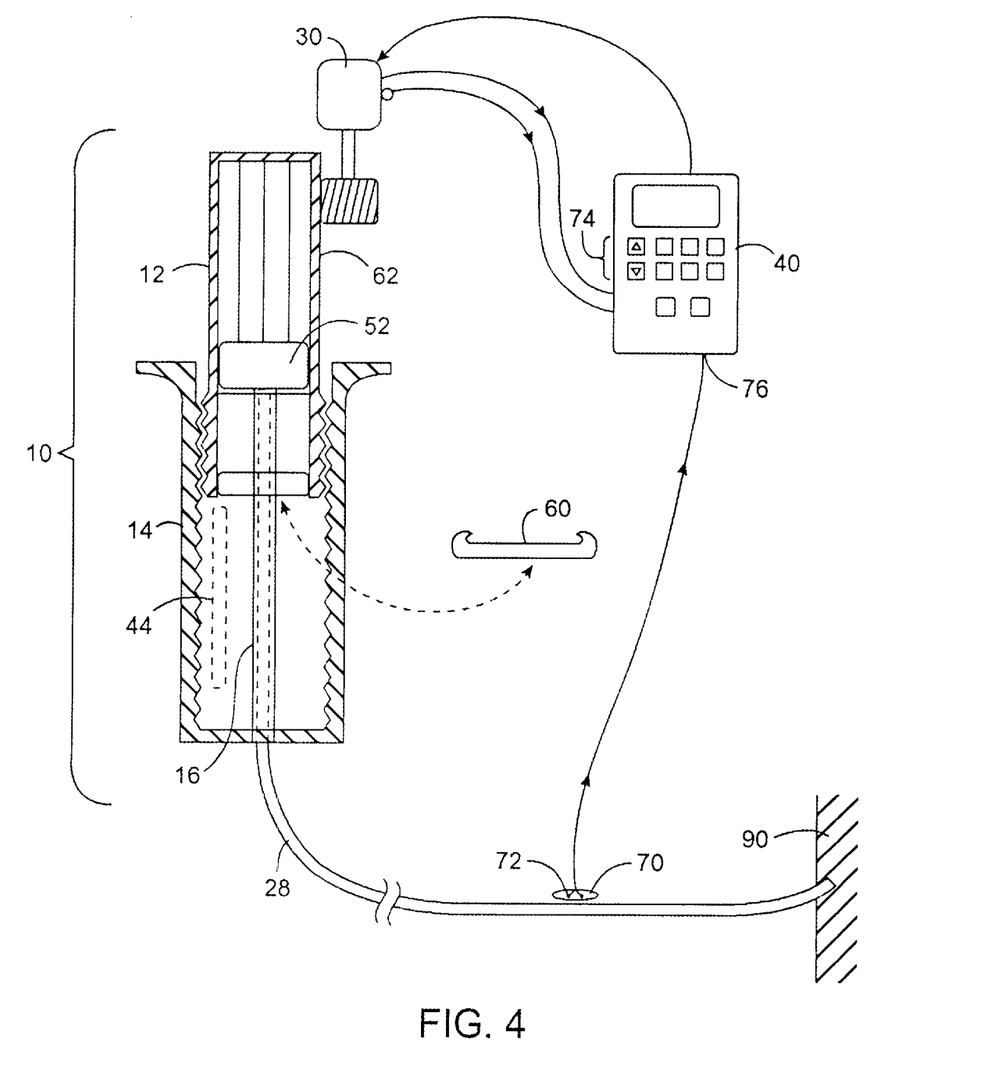
FIG. 4 is a perspective view of another preferred embodiment of the medical infusion and aspiration device.

FIG. 4 shows an alternate embodiment of the cassette 10. In this embodiment, the cassette 10 has only one opening, wherein the plunger 16 also acts as the locking system to the infusion tube 28. It is preferable that a standard lure lock attachment be included in the plunger as a single piece. A protective cap 60 is shown removed from the single piece cassette. Splines 62 on the side of the cassette 10 mesh with the gearing mechanism driven by the motor 30, all of which are attached to the pumping device 40. The motor 30 rotates the cassette 10 by attachment to splines 62 on the side, with the housing 14 fixed to the pumping device. The plunger 16 then rotates, due to the lands and groves meshed between the housing 14 and cartridge 12.

Figure 5:
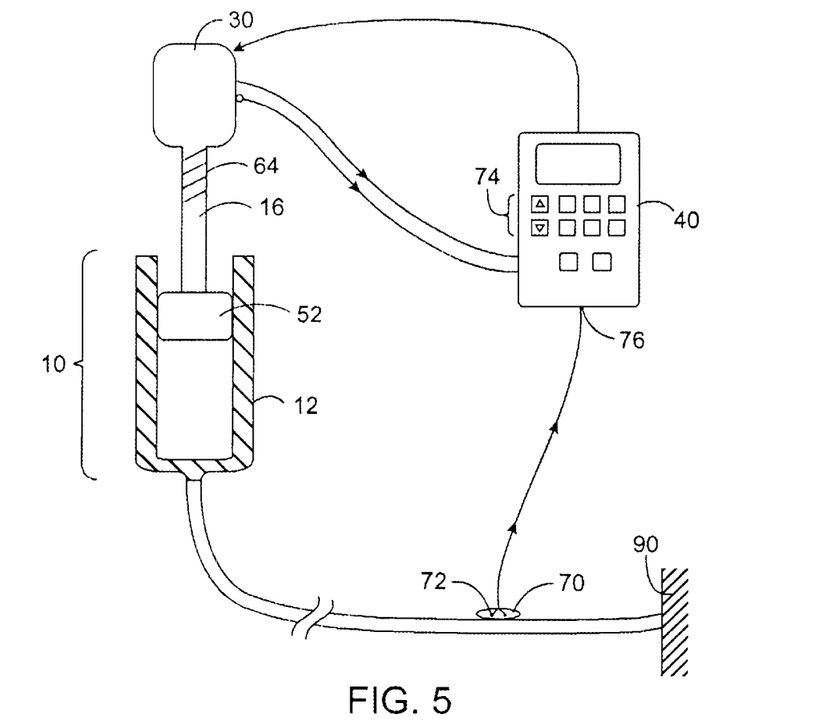
FIG. 5 is a perspective view of a third preferred embodiment of the medical infusion and aspiration device.

FIG. 5 shows another embodiment of the present invention. In this embodiment, a direct screwing system 64 interface is attached to the side of the cassette 10. The direct screwing system 64 accomplishes the rotational and axial movement required to provide the delivery profile, as well as an internal rotational drive which automatically causes the plunger 16 to turn as the motor advances the plunger 16 upwards and downwards in order to infuse or aspirate.

Figure 6:
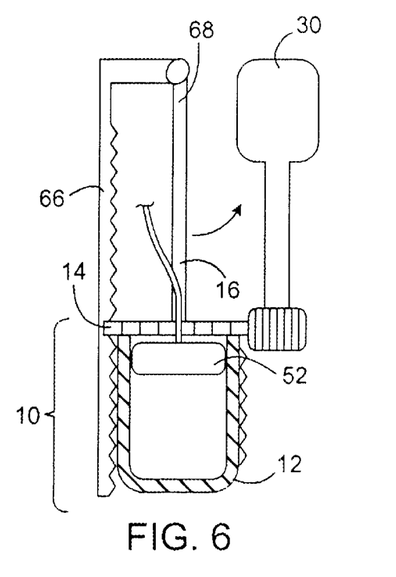
FIG. 6 is a perspective view of a fourth preferred embodiment of the medical infusion and aspiration device.
Figure 7:
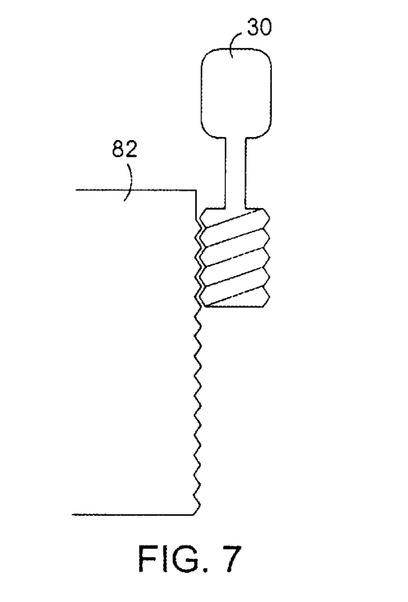
FIG. 7 is a perspective view of a fifth preferred embodiment of the medical infusion and aspiration device.

FIG. 6 shows a fourth embodiment of the present invention. FIG. 6 shows a rack 66 threaded surface, which allows the motor 30, when placed adjacent to the rack 66, to turn the housing 14. The plunger 16 remains stationary in relation to the motor 30 and rack 66, thereby causing the plunger 16 to move rotationally in reference to the cassette 10. The plunger sanction 68 may swing away for easy snap-in and snap-out action. FIG. 7 shows a fifth preferred embodiment of the present invention. FIG. 7 shows a side screw 82 configuration for the cassette.

In the preferred embodiment, the cartridge 12, when placed in the housing 14, causes the piston plunger 16 to move both forward and aft to aspirate or infuse, as well as rotate within the cassette 10 to break the forces of inertia and slip-stick as well as eliminate backlash. Because the device avoids slip-stick, chatter and the forces of hysteresis, and has no gates or valves, it is designed to also be used in a bi-directional application, such as one of the preferred embodiments herein, where the precise amount being withdrawn may be distributed, equally or in successive steps of precise delivery, or the precise amount withdrawn re-inserted into the patient to the "zero" point.

In the preferred embodiments shown in FIGS. 1, 4, and 5, a sensor area 70 is located within the infusion tube 28. The sensor area 70 contains probes 72 designed to determine the chemical components and levels of desired substrates in the aspirated fluids. The information obtained by the probes 72 relayed to the pumping device 40 and is used to control or limit the infusion profile. In prototype construction the probes were made of electromagnetic material, however any probe capable of relaying information to the pumping device may be used.

The bi-directional accuracy of the present invention allows the system to be used with any number of probes. It is preferable that the probes measure the properties of a sample, such as blood, and then allow the prevent invention to re-infuse that sample back into the patient after it has been tested, or if desired, by second flow direction, deposit that blood into a separate container or depository.

Referring to FIGS. 1, 4 and 5, the present invention also includes a pumping device 40. The pumping device 40 preferably has one, two, three or more sources of input. The preferred pumping device includes, but is not limited to, an input system to drive the device 74, a sensor input for in-line measurement of substrates 76, an in-line occlusion pressure sensing system 78 and/or input from the reading of the encoded area 80. The sensor input 76 receives signals from the in-line sensor probes 72. The in-line occlusion pressure sensing system 78 determines the line pressure or back pressure on the motor. Other traditional pump features are intended to be incorporated into the pumping device 40.

In the preferred embodiment, the Rotational Velocity exceeds the Axial Velocity, although with sufficient diameter the difference in Rotational travel to Axial travel could be adjusted for the flow characteristics of the fluid to be infused and aspirated.

Figure 8:
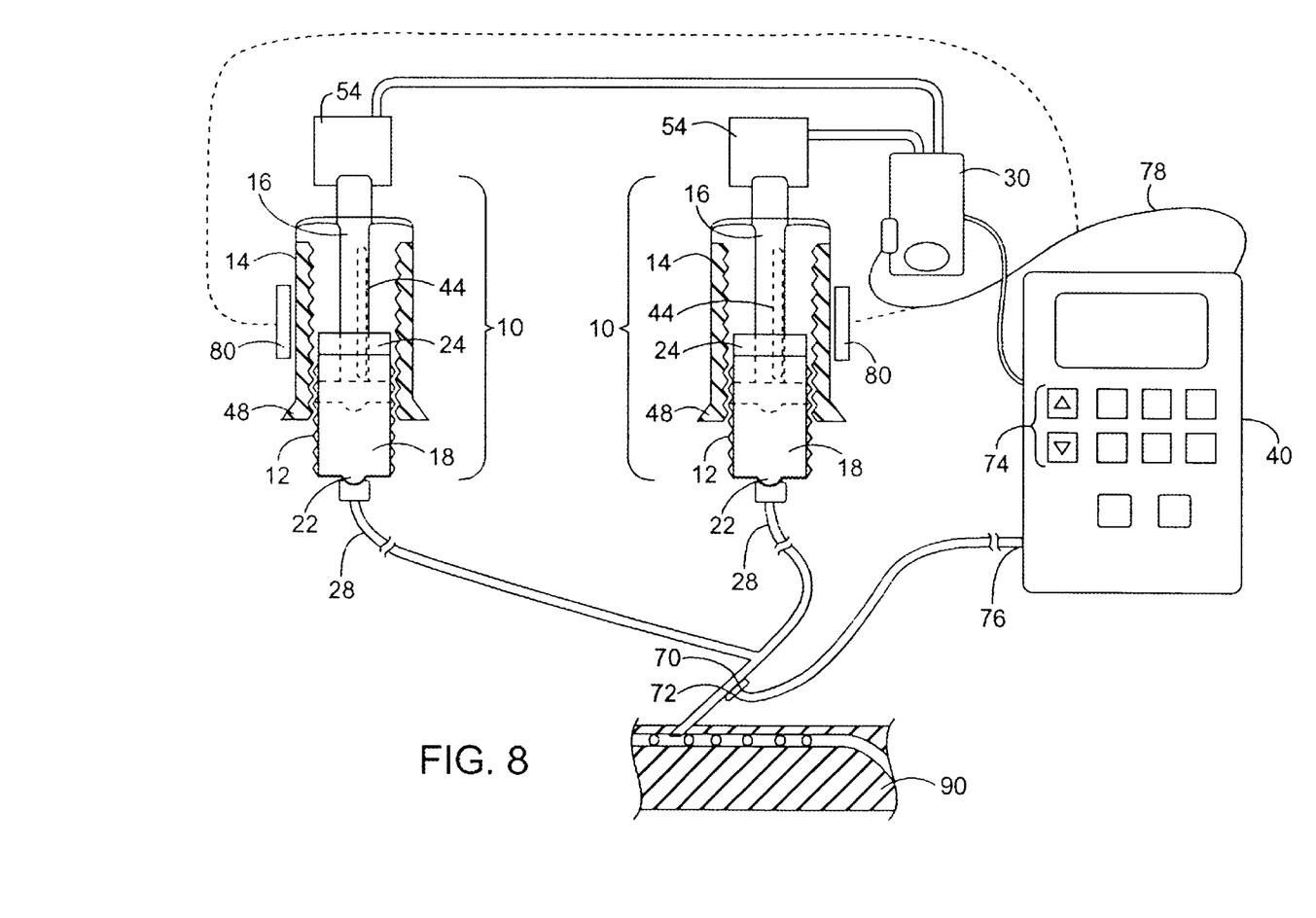
FIG. 8 is a perspective view of an embodiment of the medical infusion and aspiration system having two cassettes being driven independently.
Figure 9:
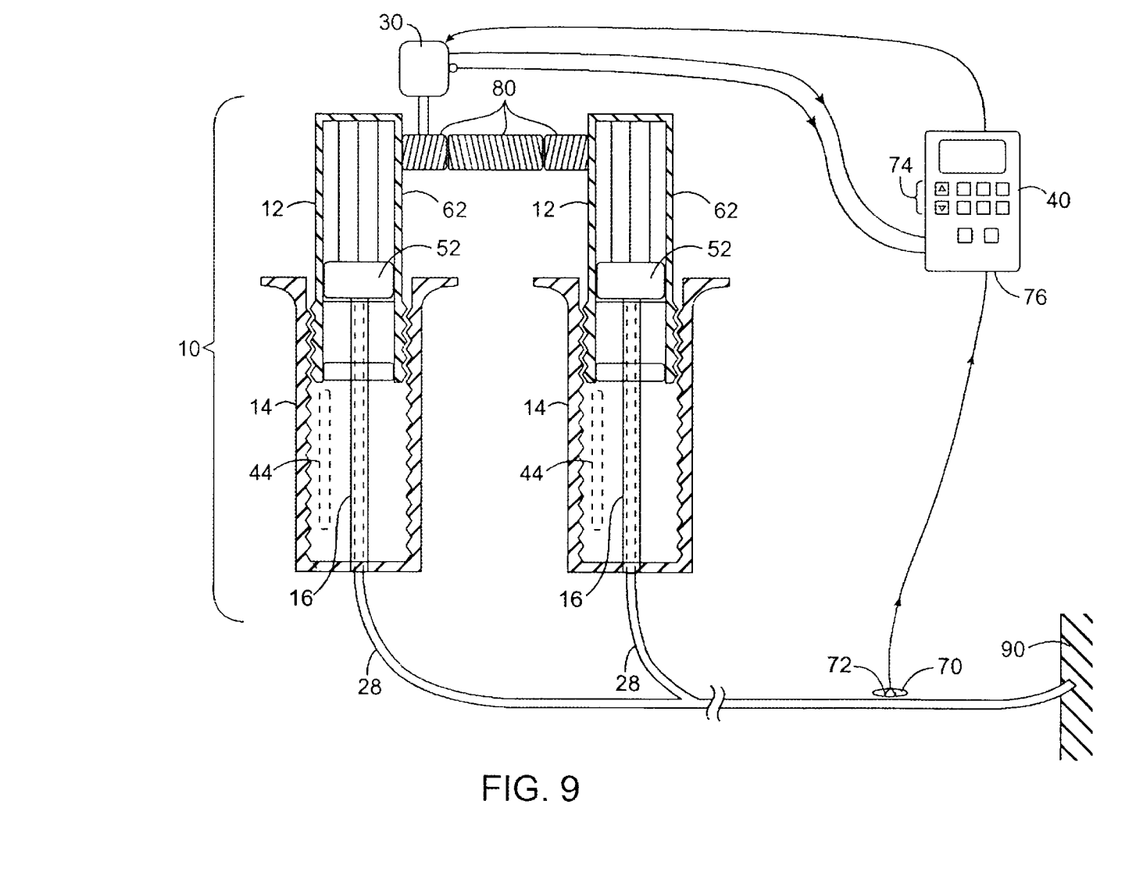
FIG. 9 is a perspective view of an embodiment of the medical infusion and aspiration system having two cassettes coupled by mechanical linkage.

It is preferable that a second cassette and housing may be coupled and driven either independently or in mechanical linkage 80 with a cassette housing so as to have as many infusion profiles, either in succession or concurrently as is desired for the given flow profiles and applications, as shown in FIGS. 8 and 9.

It is a desired effect of the present invention that certain deliveries via long catheters positioned in the patient may benefit from a very stable and accurate system which is not subject to the errors of conventional pumps, even when overcoming higher pressures within a given area.

Since the cartridge is also the pumping system, each time the cartridge is used, it is replaced, and the entire wearing aspects of the pumping system are replaced, thereby causing the product life cycles to be much greater. The entire fluid handling system is replaced with each use and sterilization and cleaning of parts is eliminated.

The purpose of the present invention is to provide a system of quantitative chronoendocrinology, a term coined by the inventor. The apparent benefit to having pulses of almost any medicine, as an additional means for delivery, was deemed by the Inventors to be a valid approach to medical infusion for any and perhaps all forms of infusion therapy. Part of the invention claimed is the use of the device in sequence of infusions which, while in the aggregate the amount medicine used is less, but by virtue of he pulses, accomplishes additional medical results.

The preferred embodiments described herein are illustrative only, and although the examples given include many specificity's, they are intended as illustrative of only a few possible embodiments of the invention. Other embodiments and modifications will, no doubt, occur to those skilled in the art. The examples given should only be interpreted as illustrations of some of the preferred embodiments of the invention, and the full scope of the invention should be determined by the appended claims and their legal equivalents.

What is claimed is:

1. A medical infusion and aspiration system for accurate pulsatile delivery, the medical infusion and aspiration system comprising:
   at least one cassette having a cartridge, a housing and a plunger, the cartridge having a cylindrical shape, an outer cartridge surface, a reservoir area, and a neck opening; the outer cartridge surface having a threaded surface and an encoded area; the housing having a bottom surface, a central axis and an inner threaded surface,
   an infusion tube,
   a pumping mechanism having a gear linkage, a motor and a pumping device, and
   an in-line sensor probe.

2. The medical infusion and aspiration system of claim 1, wherein the outer cartridge surface is in threaded relationship to the housing inner threaded surface.

3. The medical infusion and aspiration system of claim 1, wherein the infusion tube is connectively coupled to the neck opening.

4. The medical infusion and aspiration system of claim 1, wherein the cartridge is configured to receive a cap and a container top.

5. The medical infusion and aspiration system of claim 1, wherein the housing has a plurality of openings parallel to the central axis of the housing; the plurality of openings allows for trapped air to be exhausted and creates an inspection window.

6. The medical infusion and aspiration system of claim 1, wherein the bottom surface of the housing has a lip to receive a removable cover.

7. The medical infusion and aspiration system of claim 1, wherein the encoded area comprises an optical or electromagnetic strip.

8. The medical infusion and aspiration system of claim 1, wherein the plunger is aligned with the central axis of the housing and configured to fit within the reservoir area.

9. The medical infusion and aspiration system of claim 1, further comprising a mechanism capable of reading the encoded area.

10. The medical infusion and aspiration system of claim 1, wherein the gear linkage connectively couples the motor to the piston or to the housing outer surface.

11. The medical infusion and aspiration system of claim 10, wherein the motor causes a lateral and axial rotation of the plunger.

12. The medical infusion and aspiration system of claim 11, wherein the lateral and axial rotation of the plunger is bi-directional.

13. The medical infusion and aspiration system of claim 1 wherein the in-line sensor probe is located in the infusion tube.

14. The medical infusion and aspiration system of claim 13, wherein the in-line sensor probe determines a chemical component and a level of substrates in an aspirated fluid.

15. The medical infusion and aspiration system of claim 1, wherein the pumping device has at least one source of information input.

16. The medical infusion and aspiration system of claim 1, wherein the at least one cassette comprises at least two cassettes.

17. The medical infusion and aspiration system of claim 16, wherein the at least two cassettes are coupled and driven independently or in mechanical linkage.

* * * * *